United States Patent [19]

Talish et al.

[11] Patent Number: 5,186,162

[45] Date of Patent: Feb. 16, 1993

[54] ULTRASONIC TRANSDUCER DEVICE FOR TREATMENT OF LIVING TISSUE AND/OR CELLS

[75] Inventors: Roger J. Talish, Fairfield; Arthur L. Lifshey, East Brunswick, both of N.J.

[73] Assignee: Interpore Orthopaedics, Inc., West Caldwell, N.J.

[21] Appl. No.: 628,403

[22] Filed: Dec. 17, 1990

Related U.S. Application Data

[63] Continuation-in-part of Ser. No. 247,105, Sep. 14, 1988, Pat. No. 5,003,965.

[51] Int. Cl.$^5$ .............................................. A61B 17/56
[52] U.S. Cl. ................................................. 128/24 AA
[58] Field of Search ....... 73/644; 128/24 AA, 24 EL, 128/662.03, 660.10

[56] References Cited

U.S. PATENT DOCUMENTS

| | | | |
|---|---|---|---|
| 3,608,553 | 9/1971 | Balamuth | 128/24 AA |
| 4,059,098 | 11/1977 | Murdock | 73/644 |
| 4,296,753 | 10/1981 | Goudin | 128/662.03 |
| 4,708,127 | 11/1987 | Abdelghani | 128/24 AA |
| 4,909,240 | 3/1990 | Helmreich et al. | 128/24 AA |
| 4,917,096 | 4/1990 | Englehart | 128/660.1 |

Primary Examiner—Ruth S. Smith
Attorney, Agent, or Firm—Hopgood, Calimafde, Kalil, Blaustein & Judlowe

[57] ABSTRACT

The invention contemplates an improved body-applicator unit forming a component of an ultrasonic bone-therapy system exemplified by the disclosure of copending patent application Ser. No. 247,105, filed Sep. 14, 1988 now. U.S. Pat. No. 5,003,965. The improvement features transducer suspension from the rest of the applicator unit via a molded sylphon-bellows element of softly compliant elastomeric material, wherein the transducer is a flat disc, retained as the outer closure wall of the elastomeric bellows, in such manner as to be surrounded by a flexible gel-retaining circumferential lip formation of the bellows.

19 Claims, 2 Drawing Sheets

ULTRASONIC TRANSDUCER DEVICE FOR TREATMENT OF LIVING TISSUE AND/OR CELLS

RELATED CASE

This application is a continuation-in-part of copending application Ser. No. 247,105, filed Sep. 14, 1988, (now U.S. Pat. No. 5,003,965) the disclosure of which is hereby incorporated by reference.

BACKGROUND OF THE INVENTION

The invention relates to use of ultrasonic radiation at relatively low levels into living tissue, as for the non-invasive healing treatment of bone fractures, pseudarthroses and the like.

Duarte U.S. Pat. No. 4,530,360 describes a technique of treating bone defects of the character indicated using a pulsed radio-frequency ultrasonic signal applied via a transducer to the skin of a patient and directed to the site of the defect. The radio-frequency signal is in the range of 1.3 to 2 MHz, and it consists of pulses at a repetition rate of 100 to 1,000 Hz, with each pulse having a duration in the range 10 to 2,000 microseconds. The Duarte apparatus comprises a radio-frequency oscillator connected to a driver, and a pulse generator is arranged to control driver output in accordance with a preselected duration and repetition rate of bursts of radio-frequency oscillations in the driver output. A flexible radio-frequency cable connects driver output to a body applicator, in the form of a hand-held plastic tube, one end of which is closed to mount a piezoelectric transducer, in the form of a thin flat disc, excited for thickness resonance.

Necessarily, therefore, in the Duarte apparatus, the source of electrical energy is remote, as on a table top, and the flexible connection to the body applicator must, in use, always be electrically "live" and, therefore potentially hazardous. Also, for the power levels involved, and considering the fact that two or more transducers seldom can be found to resonate at precisely the same frequency, the radio-frequency must be pretuned to serve one and only one transducer. In other words, apparatus of the Duarte patent necessarily dedicates the remote signal-generating part of the system to the particular applicator. And any attempt to replace a damaged applicator must involve a retuning of the signal-generator to the newly substituted applicator.

SUMMARY OF THE INVENTION

It is an object of the invention to provide improved body-applicator apparatus, for use in an ultrasonic device, as of the character disclosed in said copending patent application.

A specific object is to provide an improved body applicator which lends itself to treatment of damaged bone tissue, as within an orthopedic cast, or as in a strapped application to a body part, featuring greater ease of application to the body part, as well as enhanced effectiveness of ultrasonic therapy.

The invention meets the above objects by providing, in an ultrasonic bone-therapy system of the character disclosed in said copending patent application, an improved body-applicator unit wherein different structure for transducer support not only lends itself to softly compliant adaptation to the local contour of an afflicted limb, but also assures retention of a gel as the medium of ultrasonic coupling between the transducer and the body locale via which directed ultrasonic energy is delivered to nearby bone tissue. The transducer is suspended from the rest of the applicator unit via a molded sylphon-bellows element of softly compliant elastomeric material, wherein the transducer is a flat disc, retained as the outer closure wall of the elastomeric bellows, in such manner as to be surrounded by a flexible gel-retaining circumferential lip formation of the bellows.

BRIEF DESCRIPTION OF THE INVENTION

The invention will be described in detail in conjunction with the accompanying drawings, in which.

DETAILED DESCRIPTION OF THE PREFERRED EMBODIMENTS

Figure 1:
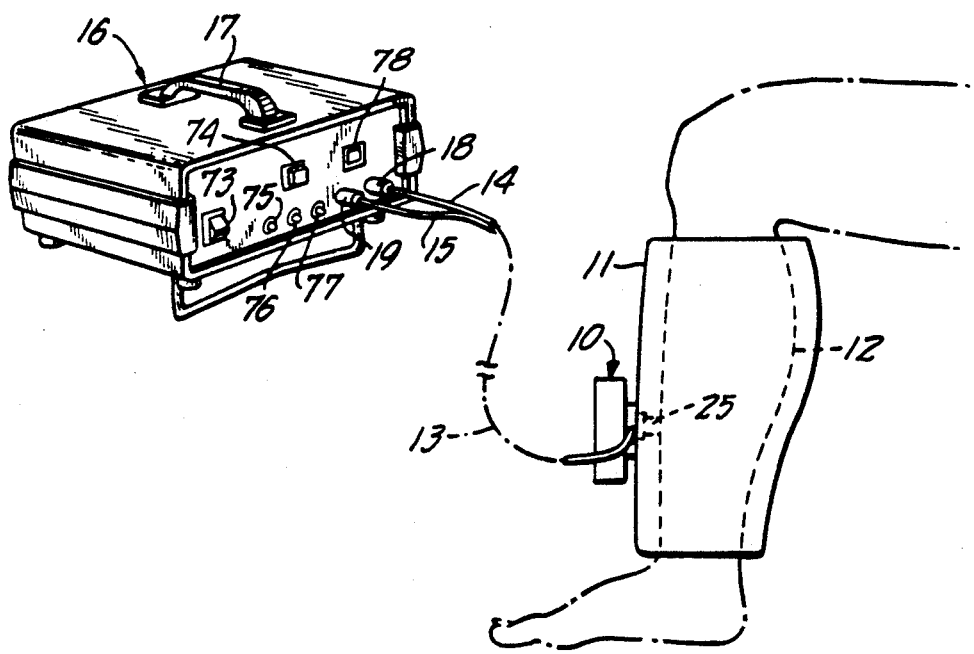
FIG. 1 is an overall view of flexibly connected remote-control and body-applicator units of the invention, in the context of providing ultrasonic treatment to damaged bone tissue within an orthopedic cast.

In FIG. 1, a body-applicator unit (or treatment head) 10 of the invention is shown mounted to an orthopedic cast 11 for treatment of a bone injury or defect in a human leg 12. A flexible cable 13 comprising separately sheathed fiber-optic lines 14, 15 connects the body-applicator unit 10 to a remote-control unit 16, which may be relatively compact and portable, as suggested by a carrying handle 17; and detachable connectors 18, 19 of optical-transmission lines 14, 15 plug into the front panel of remote-control unit 16.

Figure 2:
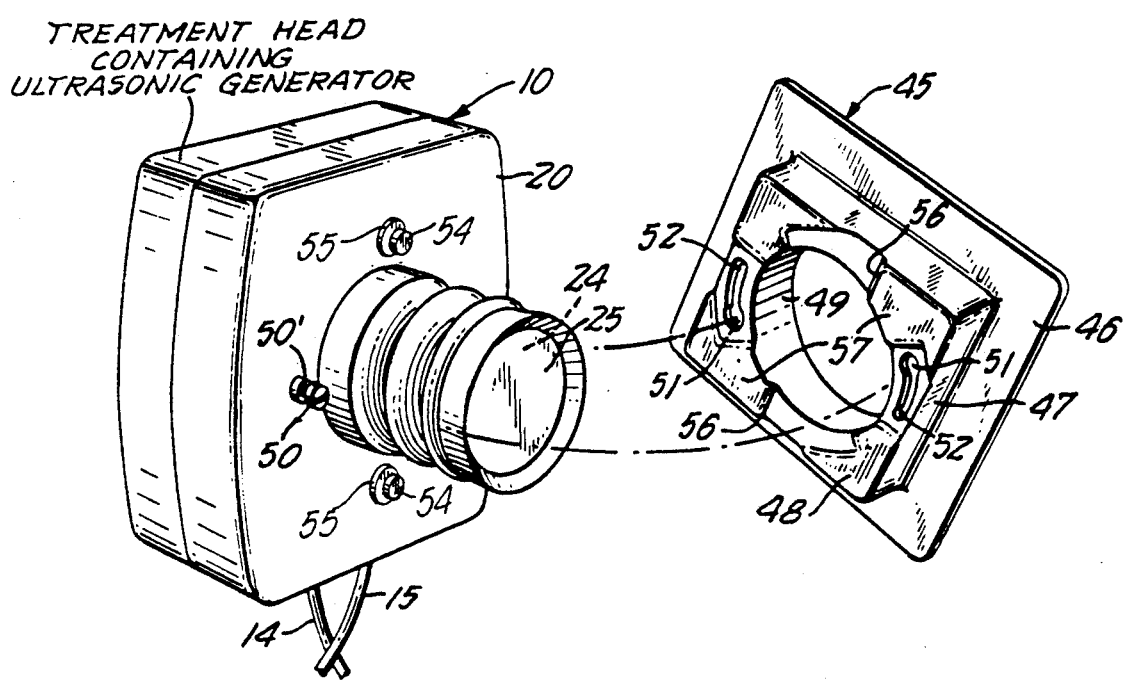
FIG. 2 is an enlarged view in one perspective of the body-applicator unit of FIG. 1 and in an image-reversed perspective of an embedment fixture, said fixture being for embedment in the cast of FIG. 1 and for detachable mounting reception of the body-applicator unit.
Figure 3:
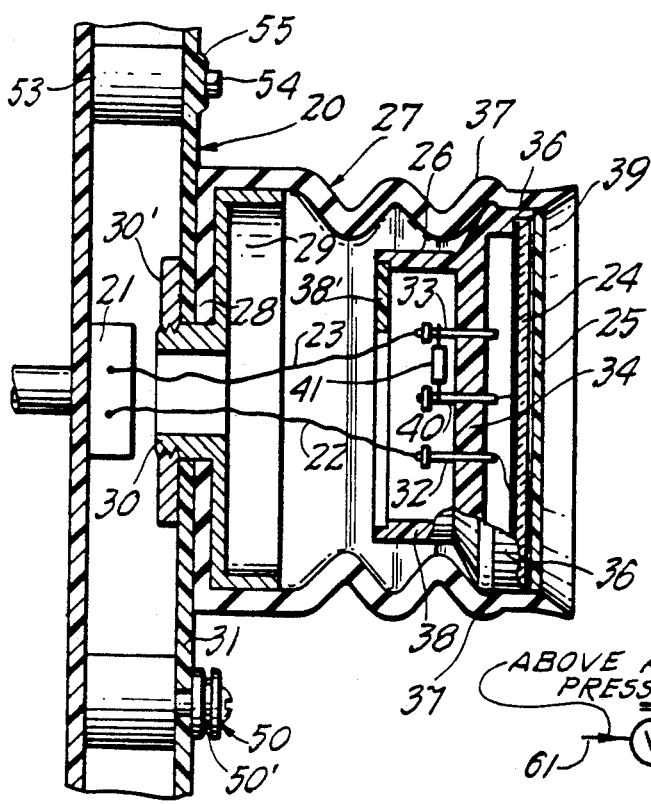
FIG. 3 is a fragmentary section which includes the central axis of the transducer and its support, in the body-applicator unit of FIGS. 1 and 2, the section half above the central axis and the section half below the central axis being taken in separate orthogonally related planes which intersect along the central axis.

The electrical contents, within the housing 20 of the body-applicator unit 10, are described in detail in said copending patent application, but it suffices, for present purposes and in the additional context of FIGS. 2 and 3, to state that housing 20 contains storage batteries and a circuit board 21 of oscillator/driver components (sometimes referred to as the ultrasonic generator), with flexible shielded-lead connections 22, 23 to a thin flat transducer element 24. Element 24 may be a commercially available piezoelectric ceramic disc, as of the lead-zirconium-titanate material known as PZT-4. Element 24 will be understood to include a separate foil electrode bonded to each of its front and back surfaces, to enable thickness fluctuation in response to driven excitation via leads 22, 23. Transducer 24 is coated with an outer protective layer 25 of epoxy and is otherwise part of a permanently sealed component 26 that is secured to the outer end of a flexible sylphon-type bellows 27, of molded softly compliant elastomeric material; use of the expression "sylphon" is intended to identify bellows 27 as generally conforming to a longitudinally extending, radially undulating figure of revolution about the central axis of bellows 27. As seen in FIG. 3, the base or mounting end of bellows 27 has an integrally formed radially inward flange 28, and a cupped clamp member 29 conforms to the inner contour and reinforces the base end of bellows 27, with a threaded hub 30 extending through a mount opening in the face panel 31 of housing 20; a nut 30' engaged to hub 30 is the means of securely clamping the base end of bellows 27 to housing 20, with flexible leads 22, 23 extending through the bore of hub 30, for connection of circuit board 21 to the respective transducer terminals 32, 33 which are exposed at the inner panel board 34 of component 26.

Specifically, the component 26 into which transducer 24 is integrated comprises a rugged molded-plastic housing, characterized by a radially outer axial flange 35 which is formed with a short counterbore, for seated location of the transducer (24) disc in axial offset from panel 34. The epoxy layer 25 which seals and protects the front face of the transducer also radially laps the axially outer end of flange 35 and completes the sealed integration of the transducer into component 26. The radially outer contour of flange 35 is characterized (1) by a cylindrical land 36 which is bonded to an outer cylindrical bore of the compliant bellows 27, and (2) by a circumferentially continuous radially outward rib or lip 37 having axially locating engagement with a similarly contoured locating groove that is a molded feature of the bore of bellows 27. Description of component 26 is completed by identifying a reduced cylindrical flange 38 which extends axially inward and which performs a protective function for terminals 32, 33 and the region of their connection to leads 22, 23; a closure panel 38' with a central opening for leads 22, 23 is affixed to close flange 38 after leads 22, 23 have been connected to their respective terminals. The radially reduced nature of flange 38 will be seen to provide generous clearance with the undulating inner contour of bellows 27, regardless of the axially compressed or angularly deflected orientation of transducer 24 with respect to its normally parallel and axially offset relation to the base mounted end of bellows 27.

The circumferentially continuous undulating outer contour of bellows 27 matches undulations of the inner contour, and a circumferentially continuous lip 39 of tapering section is an integral feature of bellows 27, being radially and axially outwardly flared for self-adapting local conformation to the body limb locale to which it is applied. Such local conformation to a body contour will be seen to enhance the prospect of circumferentially continuous lip (39) engagement to the body and to assure a self-retaining volumetric enclosure for sound-transmitting gel or liquid that must acoustically couple the transducer to subcutaneous body fluids relied upon for acoustic coupling to nearby bone structure.

Description of the transducer and its mounting structure is completed by identifying a binding post 40 additionally carried by panel 34. On the transducer side of panel 34, the binding post 40 will be understood to connect to the other foil electrode surface of the transducer; and on the axially inner face of panel 34, an inductive coil element 41 will be understood to connect post 40 to the second terminal 33. The coil element 41 will further be understood to have been selected for its ability to tune the particular transducer 24; once thus selected, prior to sealed completion of component 26, the inductive element 41 will have been custom-matched to the transducer 24, and the relationship is one of permanence, as between these "matched" elements, for a given assembly of component 26.

Figure 4:
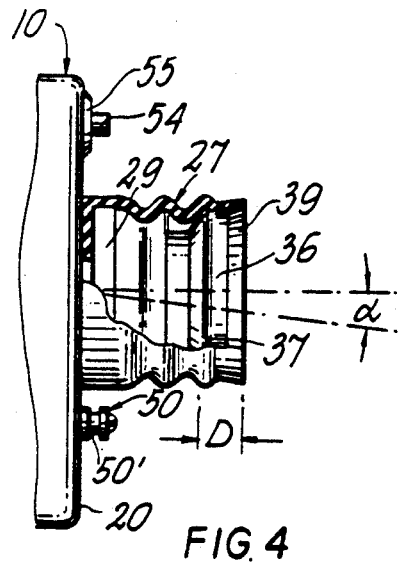
FIG. 4 is a fragmentary side view in elevation, for the aspect of FIG. 3, to show transducer accommodation to a body surface.

In the diagram of FIG. 4, the symbol D will be understood to suggest that, upon body contact, transducer 24 (and the outer body-contacting lip 39) will be deflected axially inward, with respect to housing 20. Such deflection can also be one of axial misalignment, to a self-adapting misalignment angle $a$, wherein the front face of the transducer will be understood to be no longer normal to the central axis of the base-mounting end of bellows 27.

In FIG. 2 and at spaced locations about the base end of the mounted bellows 27, housing 20 is provided with means for coaction with corresponding features of an expendable mounting fixture 45, which may be of injection-molded plastic but which can also be suitably formed by thermal slumping from plastic sheet material of suitable gauge. Fixture 45 is expendable because it is designed for embedded incorporation in an orthopedic cast, as at a locally cut access opening in stockinette, prior to development of the retaining plaster of the cast.

As shown in FIG. 2, fixture 45 is of generally rectangular outline, providing an outward flange 46 which extends peripherally around a truncated-pyramid wall 47 which positions its truncation face 48 for confronting acceptance of and removably retained engagement with the transducer-supporting side of the body-applicator unit 10. The offset extent of face 48 from flange 46 is in the order of one centimeter, to enable adequate building of casting plaster above flange 46.

The center of face 48 is characterized by an opening defined by an integrally formed cylindrical flange 49 for radially clear telescopic acceptance of the transducer-mounting bellows 27 of unit 10. The preferred engagement to unit 10 is of bayonet-locking variety, being shown on housing 20 to comprise two outwardly projecting studs 50 at diametrically opposite but radially equal offset locations on housing 20, with respect to the central axis of the projecting bellows 27. Studs 50 are enterable into diametrically opposite enlarged openings 51, at corresponding ends of arcuate and narrowed slots 52; and studs 50 are circumferentially grooved at 50' to accommodate local fixture thickness at face 48. Thus, once studs 50 are inserted at 51, unit 10 may be bodily rotated with respect to fixture 45 to complete the bayonet-locking engagement of studs 50 to slots 52.

The upper half-section of FIG. 3 additionally shows that, at diametrically opposite locations which are at 90°-offset from studs 50, the transducer side of housing 20 also mounts two normally open switches 53 having actuator buttons 54 which project outwardly but which, upon inward depression (as when the bayonet-locking engagement is effected) will close their respective contacts. These contacts will be understood to provide a safety-interlock feature, operative upon circuitry within unit 10, whereby no power can be supplied to the oscillator/driver in the absence of concurrent closure of both switches 53.

To assure frictional retention of the bayonet-locked engagement, FIGS. 2 and 3 show switch actuator buttons 54 to project beyond local land formations 55 of housing 20, and these land formations ride up cam or ramp slopes 56 to lands 57 in the face 48 of fixture 45, in the course of the relative rotation which moves studs 50 from entry openings 51 and into their other or "home" engagement positions in arcuate slots 52. After such ramping, slot-52 engagements in the grooves of studs 50 retain an axial bias of the frictional engagement between lands 55, 57.

The embodiment of FIG. 3 will be seen to establish a flexible suspension of transducer 24 wherein the volume within bellows 27 can breathe, in that the bore of bushing 30 is open to the entire inner volume of housing 20, which is not necessarily sealed. The relationship therefore accounts for relatively soft body contact when mounted to fixture 45, with ambient air pressure on both the interior and exterior surfaces of bellows 27, regardless of the extent of body-contacting deflections D and a.

Figure 5:
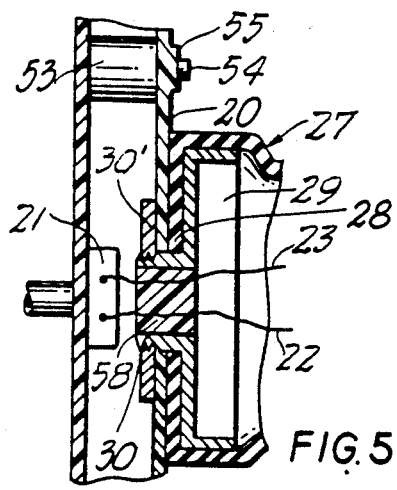
FIG. 5 is a simplified fragmentary section, generally similar to that of FIG. 3, but showing only the transducer and a modified support therefor.

In certain applications, it may be desired to establish a progressively stiffening response to increasing axial deflection D. This can be achieved by establishing a gas-sealed closure of the volume within bellows 27, as via a potting 58 which seals the leads 22, 23 and closure of the bore of bushing 30, all as suggested in the fragmentary diagram of FIG. 5.

Figure 6:
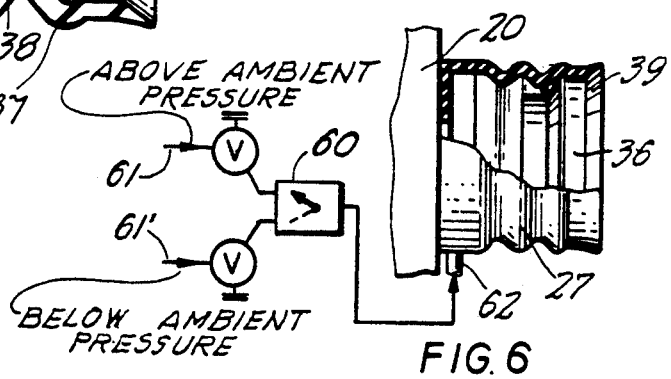
FIG. 6 is a schematic diagram which includes a simplified fragmentary section as in FIG. 5, but showing another modification.

In other applications, it may be desired to selectively apply air pressure, above and below ambient pressure, to the otherwise sealed inner volume of bellows 27. Such an arrangement is shown in FIG. 6 wherein selective control 60 supplied by dual inlet lines 61, 61' will determine (1) whether admitted air is above or below ambient pressure, and (2) the magnitude of the thus-selected control of pressure within the otherwise sealed volume of bellows 27. As shown, selected air pressure, above or below ambient, is admitted via a tube 62 removably connected to a side-port fitting at the base end of bellows 27.

Figure 7:
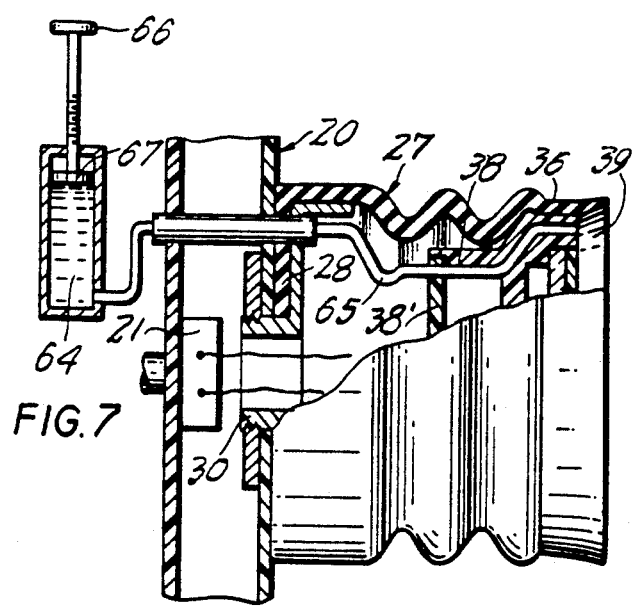
FIG. 7 is another such schematic diagram to illustrate a further modification.

In still further applications, which may involve any selected one of the foregoing conditions of controlled or uncontrolled gas pressure within bellows 27, FIG. 7 shows that provision may be made for supplying liquid or gel to the trapped volume defined by and between the transducer coating 25, the adjacent living body locale and the flexed circumferentially continuous closure effected by lip 39. As seen in FIG. 7, a supply reservoir 64 of sound-transmitting liquid or gel may be piggy-backed to the housing 20 with a flexible supply-line connection 65 via a passage through the inner wall of housing 20 or the bore of bushing 30, and thence within the volume of bellows 27 and via a local peripheral notch or otherwise-formed accommodation in the bore of bellows 27 (or in component 26), with discharge into the space within lip 39 and between the transducer coating and the body locale. In the arrangement shown, rotation of a knob 66 causes threaded advance of a feed piston 67 within the bore of reservoir 64, thereby effecting a controlled feeding advance of the liquid or gel needed for acoustic coupling at the lip-sealed region of interest. This arrangement will be seen to have particular utility for an individual who must apply his own treatment head 10 to himself, because he can always feed the gel until he is satisfied that acoustic coupling is complete, thus giving himself the best therapy that his ultrasonic equipment can deliver.

As indicated above, overall operation of the contents of applicator unit 10 and the cooperative relation with control unit 16 are available by reference to said co-pending patent application. And it is well to repeat that ultrasonic energy, delivered in bursts to transducer 24 is generally in the range 1.3 to 2.0 MHz, at a 1-KHz pulse-repetition rate, for a control-pulse duration of 200 microseconds; these values are typical and illustrative but not necessarily critical, in that, as taught by Duarte, pulse-repetition rate may suitably be in the range between 100 and 1,000 Hz, and control-pulse duration may suitably be in the range between 10 and 2,000 microseconds. Also a 20-minute treatment time will be understood to be typical, for one treatment per day, in that other treatment times and numbers of treatments per day may also be therapeutically beneficial. Generally, and desirably, the average intensity of ultrasonic energy delivered to the body is in the range of 1 to 50 milliwatts/cm$^2$.

Finally, it is well to complete a description of the front panel of control unit 16, by identifying an on/off switch 73 for placing the apparatus in readiness to operate, a "start" button 74 for initiating a treatment program, and various indicator lamps 75, 76, 77 which are indicative of current system status. For example, a "standby" lamp 75 may be amber and indicative of current operation within the treatment-time period of a preset timer (not shown); a "complete" lamp 76 may be blue and indicative of completion of the preset treatment period; and a "trouble" lamp 77 may be red and indicative of a non-compliance detection, as described in said patent application. Finally, an "active" indicator lamp at 78 may be green and indicative of readiness to commence a timed treatment.

What is claimed is:

1. For use in the treatment of living tissue and/or cells with ultrasonic radiation, a treatment-head unit comprising a housing, an ultrasonic generator contained within said housing, an ultrasonic transducer connected to said generator and having an active body-application face exposed externally of said housing, means on said housing for removably mounting the same to a living-body member with the transducer poised for delivery of active ultrasonic energy to the living-body member, said means including a compliant flexible mount projecting externally of said housing for enabling the transducer to flexibly adapt to the local living-body surface to which it is applied, said flexible mount comprising a unitary bellows of elastomeric material, said bellows having a base end secured to said housing, and said bellows having an outwardly projecting end supporting said transducer.

2. The treatment-head unit of claim 1, wherein said bellows comprises a circumferentially continuous longitudinally undulating figure of revolution about a central axis of said bellows.

3. The treatment head of claim 2, in which said transducer is a circular disc of piezoelectric material, and in which the outwardly projecting end of said bellows has a bore configuration adapted for retaining location of said transducer.

4. The treatment-head of claim 2, in which said bellows has a circumferentially continuous sealed relation to said transducer and to said housing, whereby the included volume of said bellows is characterized by an enclosed volume of air or other gas.

5. The treatment-head of claim 2, in which said bellows has a circumferentially continuous sealed relation to said transducer and in which a ported aperture is provided in the base connection of said bellows to said housing for gas flow in and/or out of said bellows in response to transducer deflection with respect to said housing.

6. The treatment-head of claim 5, in which a source of air pressure above and/or below ambient air pressure includes selectively operable control means governing air supply to the inner volume of said bellows via said ported aperture.

7. The treatment-head of claim 2, in which said bellows has a circumferentially continuous flexible lip which projects outwardly of said transducer, for body-adapting compliant conformance with a contacted body contour, and for applied-gel retention over the active body-application face of said transducer.

8. The treatment-head of claim 7, in which said lip is of tapering section, reducing in a direction which conically flares axially and radially outward of said transducer.

9. The treatment-head of claim 7, in which said lip in contact with a living body defines with said transducer an included volume circumscribed by said lip, and in which a container of ultrasonic-transmitting gel or liquid carried by said housing has a flexible-conduit connection to the transducer-supporting outer end of said bellows and with a discharge end that communicates with the included volume within said lip, and selectively operable means for advancing a flow of said gel or liquid from said container to the point of discharge into the included volume within said lip.

10. The treatment-head of claim 1, in which said transducer includes opposed electrodes and is united to a unit-handling component having electrical terminals for lead-connection to said generator, and a tuning inductor element connected to one of said terminals and to one of the electrodes of transducer for specifically adapting said transducer to an efficiently coupled relation to said generator.

11. For use in the treatment of living tissue and/or cells with ultrasonic radiation, a compliant flexible transducer-mounting assembly comprising a unitary bellows of elastomeric material extending longitudinally between a transducer-mounting end and a base-mounting end, said base-mounting end having means adapted for attachment to a rigid body, an ultrasonic transducer mounted in sealed relation to the transducer-mounting end of said bellows and oriented for longitudinally directed ultrasonic radiation beyond said transducer-mounting end, and flexible electrical leads connected to said transducer and container within said bellows and having means for external connection at said base-mounting end.

12. The assembly of claim 11, wherein said bellows is a syphon-type bellows.

13. The assembly of claim 12, in which said base-mounting end includes an integrally formed radially inward flange, a rigid circular plate is assembled within said bellows in reinforcing abutment with said flange, and in which said means of attachment is a part of said plate.

14. The assembly of claim 12, in which said bellows has a circumferentially continuous flexible lip which extends longitudinally beyond said transducer, for body-adapting compliant conformance with a contacted body contour, and for applied-gel retention between said transducer and the contacted body contour.

15. The assembly of claim 14, in which said lip is of tapering section, reducing in a direction which conically flares axially and radially outward of said transducer.

16. The assembly of claim 14, in which said lip in contact with a living body defines with said transducer an included volume circumscribed by said lip, and in which a flexible gel-supply conduit within said bellows has a discharge end at the transducer-mounting end of said bellows, said discharge end communicating with the included volume within said lip, and said conduit having a gel-supply connection at the base-mounting end of said bellows.

17. The assembly of claim 11, in which said transducer is a circular disc of piezoelectric material, and in which the transducer-mounting end of said bellows has a bore configuration adapted for peripheral retention of said transducer.

18. For use in the treatment of living tissue and/or cells with ultrasonic radiation, a flexible transducer-mounting assembly comprising a compliant unitary bellows extending longitudinally on a central axis between a transducer-mounting end and a base-mounting end, said base-mounting end having means adapted for attachment to a rigid body, an ultrasonic transducer mounted in peripherally retained relation to the transducer-mounting end of said bellows and oriented for longitudinally directed ultrasonic radiation beyond said transducer-mounting end, flexible electrical leads connected to said transducer and contained within said bellows and having means for external connection at said base-mounting end, and a peripherally continuous flexible lip formation around said transducer and projecting axially forward of said transducer for body-contour adaptation and retention of an applied gel to acoustically couple said transducer to a body portion that is surrounded by said lip formation.

19. The assembly of claim 18, in which said lip formation in contact with a living body defines with said transducer an included volume circumscribed by said lip formation, and in which a flexible gel-supply conduit within said bellows has a discharge end at the transducer-mounting end of said bellows, said discharge end communicating with the included volume within said lip, and said conduit having a gel-supply connection at the base-mounting end of said bellows.

* * * * *